(12) United States Patent
Deese

(10) Patent No.: US 8,809,806 B1
(45) Date of Patent: Aug. 19, 2014

(54) PORTABLE STERILIZATION ASSEMBLY

(76) Inventor: Bill J. Deese, Pembroke, NC (US)

( * ) Notice: Subject to any disclaimer, the term of this patent is extended or adjusted under 35 U.S.C. 154(b) by 142 days.

(21) Appl. No.: 13/290,233

(22) Filed: Nov. 7, 2011

(51) Int. Cl.
*H01J 37/20* (2006.01)

(52) U.S. Cl.
USPC ............ 250/455.11; 250/453.11; 250/454.11; 250/504 H

(58) Field of Classification Search
USPC ................. 250/453.11–455.11, 504 R, 504 H
See application file for complete search history.

(56) References Cited

U.S. PATENT DOCUMENTS

| 306,223 | A | 10/1884 | Crain |
| 3,465,761 | A | 9/1969 | Meeker et al. |
| 4,114,194 | A | 9/1978 | Walter |
| 4,456,022 | A | 6/1984 | Roberts |
| 4,474,198 | A | 10/1984 | Greenfield, Jr. et al. |
| 7,493,781 | B2 | 2/2009 | Ooe |
| 7,511,283 | B2 * | 3/2009 | Chor ........................ 250/455.11 |
| 7,754,026 | B2 | 7/2010 | Kehl |
| 2008/0099055 | A1 | 5/2008 | Lemley |

* cited by examiner

*Primary Examiner* — Michael Maskell

(57) ABSTRACT

A portable sterilization assembly includes a housing that has a bottom wall and a perimeter wall that is attached to and extends upwardly from the bottom wall. A container has an upper wall, a lower wall, and an exterior wall extending between the upper and lower walls. The exterior wall is adjoined to the perimeter wall and the bottom and lower walls are co-planar with each other. The upper wall has a pump aperture extending therethrough. A pump is mounted on the housing and extends through the pump aperture to be in fluid communication with an interior of the container. An ultraviolet light is mounted within the housing. An actuator mounted on the housing is electrically coupled to the ultraviolet light. The housing may have eating utensils inserted inside and the actuator actuated such that the ultraviolet light directs ultraviolet light into the housing to sterilize the eating utensils.

6 Claims, 6 Drawing Sheets

PORTABLE STERILIZATION ASSEMBLY

BACKGROUND OF THE DISCLOSURE

Field of the Disclosure

The disclosure relates to portable sterilizations and more particularly pertains to a new portable sterilization for sterilizing eating utensils.

SUMMARY OF THE DISCLOSURE

An embodiment of the disclosure meets the needs presented above by generally comprising a housing that has a bottom wall and a perimeter wall that is attached to and extends upwardly from the bottom wall. The perimeter wall includes an upper edge, an inner surface and an outer surface. A container has an upper wall, a lower wall, and an exterior wall extending between the upper and lower walls. The exterior wall is adjoined to the perimeter wall and the bottom and lower walls are co-planar with each other. The upper wall has a pump aperture extending therethrough. A pump is mounted on the container and extends through the pump aperture to be in fluid communication with an interior of the container. An ultraviolet light is mounted within the housing. An actuator is electrically coupled to the ultraviolet light and is mounted on the housing. The actuator actuates the ultraviolet light. A power supply is electrically coupled to the actuator and the ultraviolet light. The housing is configured to have eating utensils inserted therein and the actuator actuated such that the ultraviolet light directs ultraviolet light into the housing to sterilize the eating utensils.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
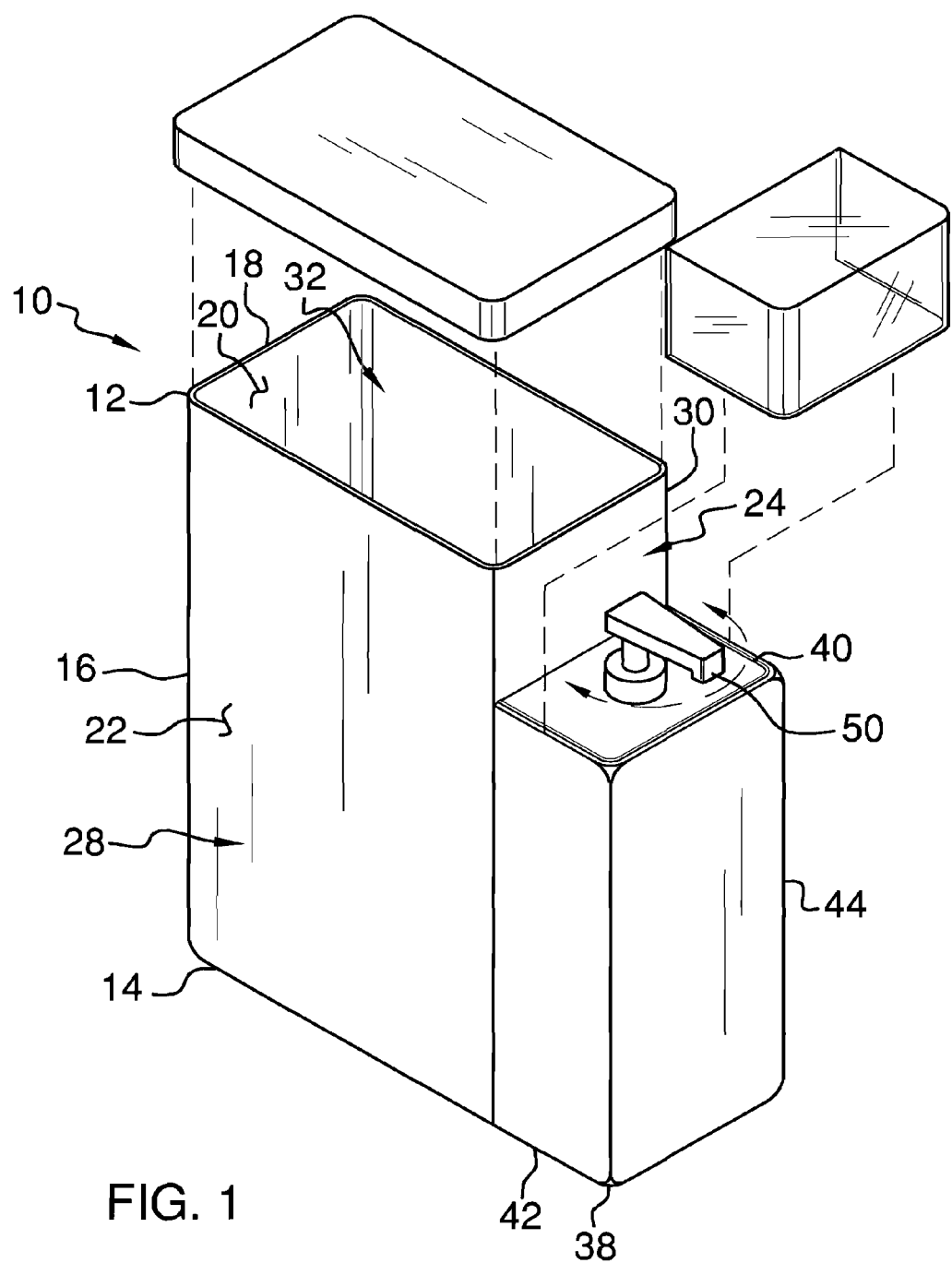
FIG. 1 is a top perspective view of a portable sterilization assembly according to an embodiment of the disclosure.
Figure 2:
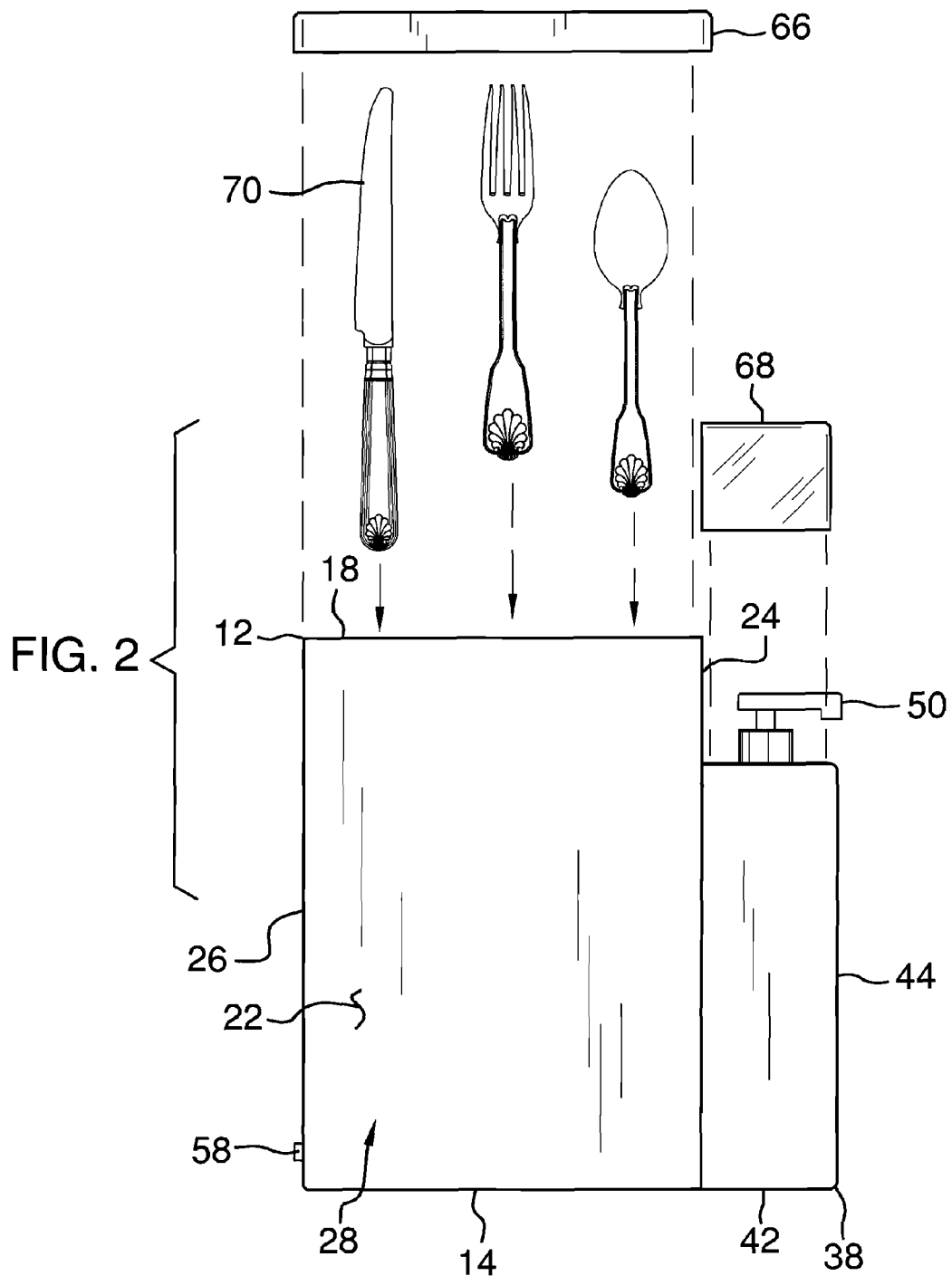
FIG. 2 is a front exploded view of an embodiment of the disclosure.
Figure 3:
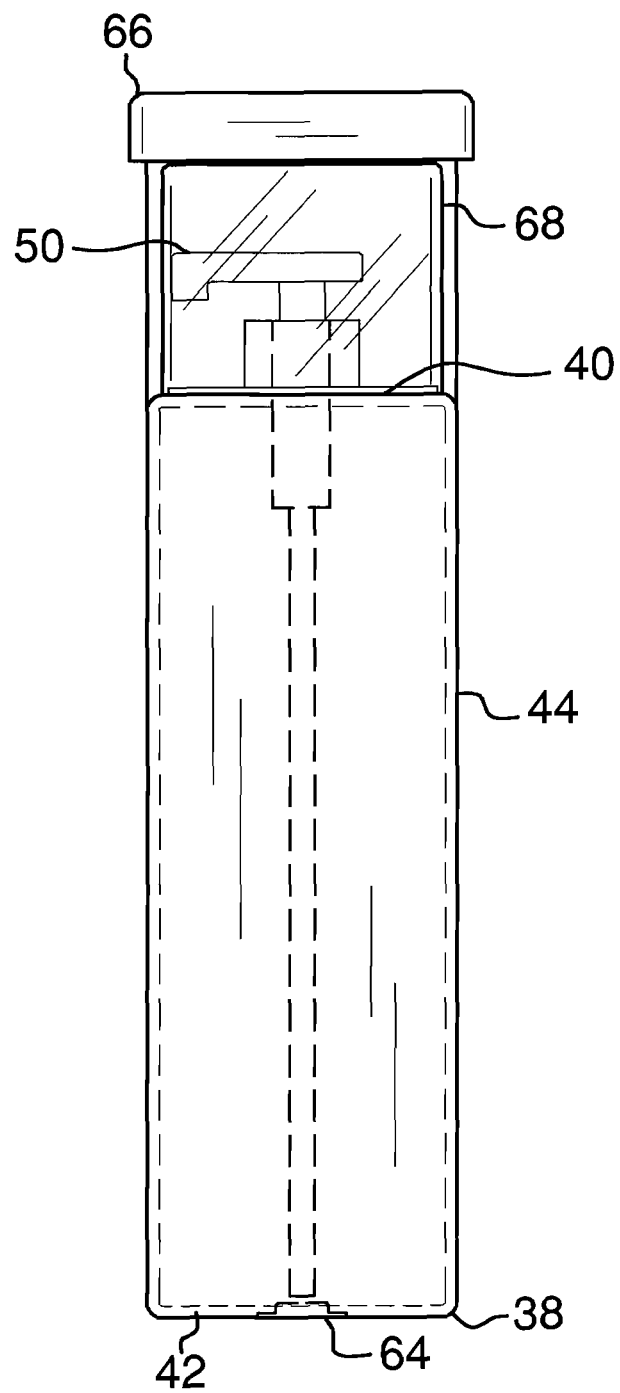
FIG. 3 is a right side phantom view of an embodiment of the disclosure.
Figure 4:
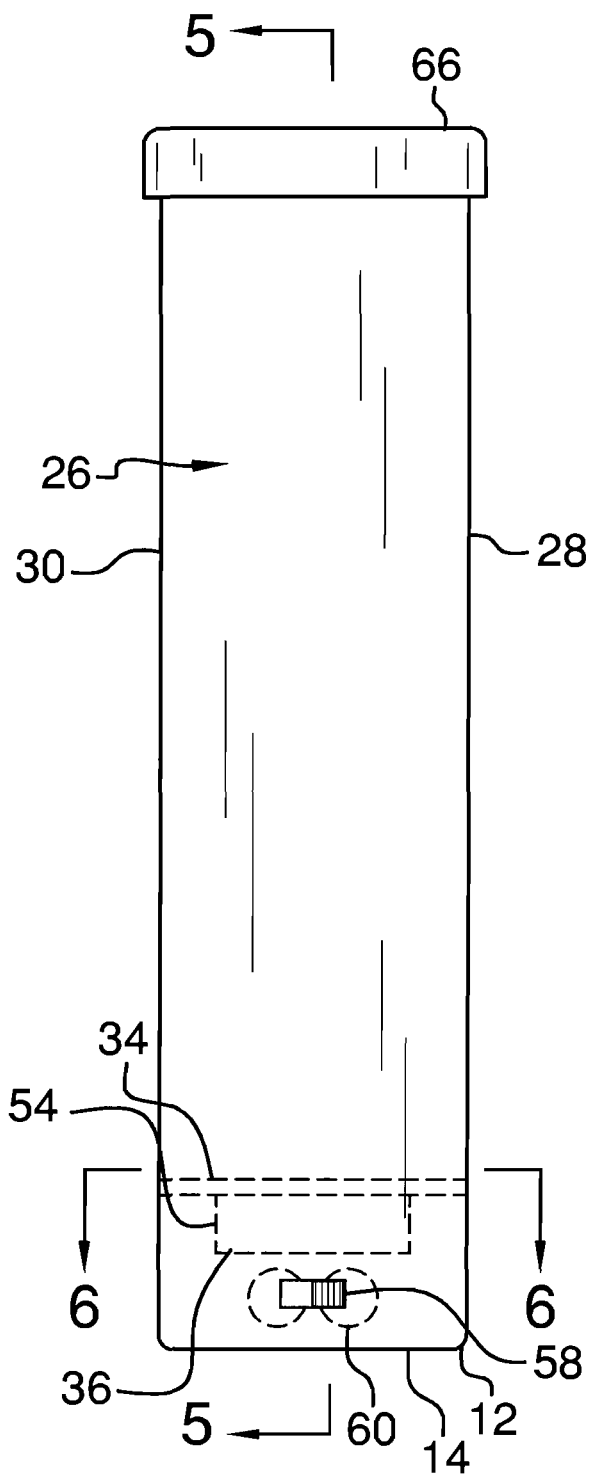
FIG. 4 is a left side phantom view of an embodiment of the disclosure.
Figure 5:
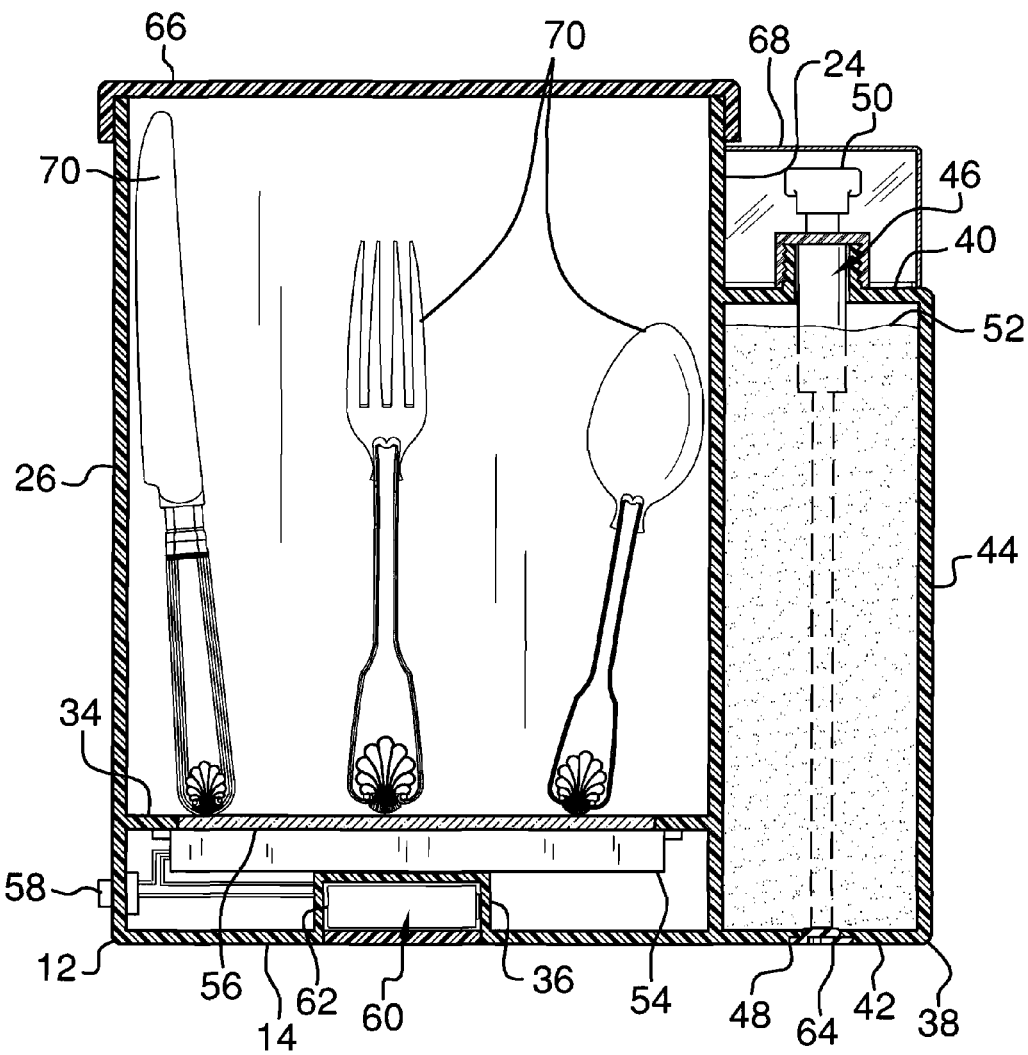
FIG. 5 is a cross-sectional view taken along line 5-5 of FIG. 4 of an embodiment of the disclosure.
Figure 6:
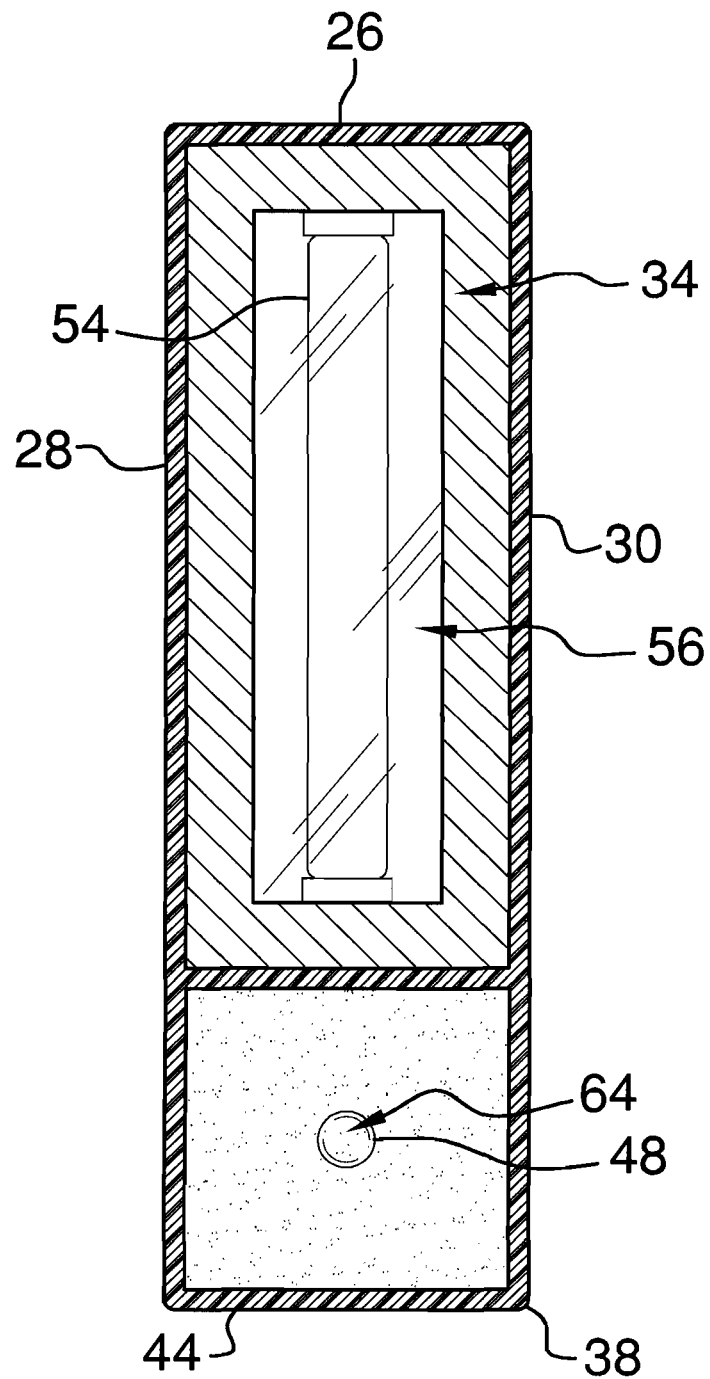
FIG. 6 is a cross-sectional view taken along line 6-6 of FIG. 4 of an embodiment of the disclosure.

With reference now to the drawings, and in particular to FIG. 1 through 6 thereof, a new portable sterilization assembly embodying the principles and concepts of an embodiment of the disclosure and generally designated by the reference numeral 10 will be described.

As best illustrated in FIG. 1 through 6, the portable sterilization assembly 10 generally comprises a housing 12 that has a bottom wall 14 and a perimeter wall 16 that is attached to and extends upwardly from the bottom wall 14. The perimeter wall 16 includes an upper edge 18, an inner surface 20, an outer surface 22, a first lateral wall 24, a second lateral wall 26, a front wall 28 and a back wall 30. The upper edge 18 defines an opening 32 to access an interior of the housing 12. The inner surface 20 has a first flange 34 attached thereto. The first flange 34 is positioned closer to the bottom wall 14 than the upper edge 18. A battery compartment 36 is positioned in the housing 12 between the first flange 34 and the bottom wall 14. The housing 12 has a length and a width that are each less than 4 inches and a height that is less than 8 inches. The housing 12 may be comprised of a rigid and lightweight material such as plastic or other similar material.

A container 38 has an upper wall 40, a lower wall 42, and an exterior wall 44 extending between the upper 40 and lower 42 walls. The exterior wall 44 is adjoined to the perimeter wall 16 and the bottom 14 and lower walls 42 are co-planar with each other. The upper wall 40 has a pump aperture 46 extending therethrough. The lower wall 42 has a drain aperture 48 extending therethrough.

A pump 50 is mounted on the container 38 and extends through the pump aperture 46 to be in fluid communication with an interior of the container 38. The pump 50 may be of any conventional design that is hand actuated. The container 38 may contain an anti-bacterial solution 52 or other similar material for sanitizing a person's hands.

An ultraviolet light 54 is mounted within the housing 12 and the ultraviolet light 54 is positioned between the first flange 34 and the bottom wall 14 to direct ultraviolet light through an opening encompassed by the first flange 34 and into the interior of the housing 12. The ultraviolet light 54 may generate a UV wavelength between 250 nanometers and 270 nanometers. The ultraviolet light 54 may subject the interior of the housing to a minimum UV radiation level of 16 milliwatts per square centimeter. A window 56 is mounted within and covers the opening defined by the first flange 34. The window 56 may be comprised of a rigid and translucent material.

An actuator 58 is electrically coupled to the ultraviolet light 54 and is mounted on the housing 12. The actuator 58 actuates the ultraviolet light. A power supply 60 is electrically coupled to the actuator 58 and the ultraviolet light 54. The power supply 60 comprises a battery 62 that is mounted in the battery compartment 36.

A plug 64 is removably inserted into the drain aperture 48. A cover 66 is removably positioned on and engages the upper edge 18 to close the housing 12. A pump lid 68 is removably positioned on and engages the upper wall 40 to cover the pump 50. The housing 12 is configured to have eating utensils 70 inserted therein and the actuator 58 actuated such that the ultraviolet light 54 directs ultraviolet light into the housing 12 to sterilize the eating utensils 70.

In use, eating utensils 70, such as provided at a public restaurant, may be placed inside the housing 12. The cover 66 may be positioned on the housing 12 and the actuator 58 may be actuated. The actuator 58 actuates the ultraviolet light 54 causing the ultraviolet light 54 to direct UV radiation into the interior of the housing 12 to sanitize the eating utensils 70. The pump 50 may be manually actuated to dispense a hand sanitizer 52 as needed.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A portable sterilization assembly configured for sterilizing eating utensils, said assembly comprising:
   a housing having a bottom wall and a perimeter wall being attached to and extending upwardly from said bottom wall, said perimeter wall including an upper edge, an inner surface and an outer surface;
   a container having an upper wall, a lower wall, and an exterior wall extending between said upper and lower walls, said exterior wall being adjoined to said perimeter wall and said bottom and lower walls being co-planar with each other, said upper wall having a pump aperture extending therethrough;
   a pump being mounted on said container and extending through said pump aperture to be in fluid communication with an interior of said container;
   an ultraviolet light being mounted within said housing;
   an actuator being electrically coupled to said ultraviolet light and being mounted on said housing, said actuator actuating said ultraviolet light;
   a power supply being electrically coupled to said actuator and said ultraviolet light; and
   wherein said housing is configured to have eating utensils inserted therein and said actuator actuated such that said ultraviolet light directs ultraviolet light into said housing to sterilize the eating utensils.

2. The assembly according to claim 1, further including said inner surface having a first flange attached thereto, said first flange being positioned closer to said bottom wall than said upper edge, said ultraviolet light being positioned between said first flange and said bottom wall and directing ultraviolet light through an opening encompassed by said flange and into the interior of said housing, a window being mounted within and covering said aperture defined by said first flange, said window being comprised of a rigid and translucent material.

3. The assembly according to claim 2, said power supply comprising a battery compartment being positioned in said housing between said flange and said bottom wall.

4. The assembly according to claim 1, said lower wall having a drain aperture extending therethrough, a plug being removably inserted into said drain aperture.

5. The assembly according to claim 1, further including:
   a cover being removably positioned on and engaging said upper edge to close said housing; and
   a pump lid being removably positioned on engaging said upper wall to cover said pump.

6. A portable sterilization assembly configured for sterilizing eating utensils, said assembly comprising:
   a housing having a bottom wall and a perimeter wall being attached to and extending upwardly from said bottom wall, said perimeter wall including an upper edge, an inner surface, an outer surface, a first lateral wall, a second lateral wall, a front wall and a back wall, said upper edge defining an opening to access an interior of said housing, said inner surface having a first flange attached thereto, said first flange being positioned closer to said bottom wall than said upper edge, a battery compartment being positioned in said housing between said flange and said bottom wall, said housing having a length and a width each being less than 4 inches and a height being less than 8 inches;
   a container having an upper wall, a lower wall, and an exterior wall extending between said upper and lower walls, said exterior wall being adjoined to said perimeter wall and said bottom and lower walls being co-planar with each other, said upper wall having a pump aperture extending therethrough, said lower wall having a drain aperture extending therethrough;
   a pump being mounted on said container and extending through said pump aperture to be in fluid communication with an interior of said container;
   an ultraviolet light being mounted within said housing, said ultraviolet light being positioned between said first flange and said bottom wall and directing ultraviolet light through an opening encompassed by said flange and into the interior of said housing;
   a window being mounted within and covering said aperture defined by said first flange, said window being comprised of a rigid and translucent material;
   an actuator being electrically coupled to said ultraviolet light and being mounted on said housing, said actuator actuating said ultraviolet light;
   a power supply being electrically coupled to said actuator and said ultraviolet light, said power supply comprising a battery being mounted in said battery compartment;
   a plug being removably inserted into said drain aperture;
   a cover being removably positioned on and engaging said upper edge to close said housing;
   a pump lid being removably positioned on engaging said upper wall to cover said pump; and
   wherein said housing is configured to have eating utensils inserted therein and said actuator actuated such that said ultraviolet light directs ultraviolet light into said housing to sterilize the eating utensils.

* * * * *